US008470903B2

(12) United States Patent
Abt et al.

(10) Patent No.: US 8,470,903 B2
(45) Date of Patent: *Jun. 25, 2013

(54) ULTRA HIGH MOLECULAR WEIGHT POLYETHYLENE ARTICLES AND METHODS OF FORMING ULTRA HIGH MOLECULAR WEIGHT POLYETHYLENE ARTICLES

(75) Inventors: Niels A. Abt, Winterthur (CH); Werner Schneider-Storrer, Rafz (CH)

(73) Assignee: Zimmer GmbH, Winterthur (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/942,703

(22) Filed: Nov. 9, 2010

(65) Prior Publication Data

US 2011/0136933 A1 Jun. 9, 2011

Related U.S. Application Data

(63) Continuation of application No. 11/465,743, filed on Aug. 18, 2006, now Pat. No. 7,846,376, which is a continuation of application No. PCT/EP2005/008967, filed on Aug. 18, 2005.

(51) Int. Cl.
*G03G 9/097* (2006.01)
*C08J 2/46* (2006.01)
*C08F 110/02* (2006.01)
*A61F 2/28* (2006.01)

(52) U.S. Cl.
USPC .......... 522/75; 522/161; 526/352; 623/23.58; 623/23.59

(58) Field of Classification Search
USPC ............... 522/75, 161; 526/352; 623/23.58, 623/23.59
See application file for complete search history.

(56) References Cited

U.S. PATENT DOCUMENTS

| | | | |
|---|---|---|---|
| 5,577,368 A | 11/1996 | Hamilton et al. | |
| 5,753,182 A | 5/1998 | Higgins | |
| 5,827,904 A | 10/1998 | Hahn | |
| 5,879,400 A | 3/1999 | Merrill et al. | |
| 6,017,975 A | 1/2000 | Saum et al. | |
| 6,087,553 A | 7/2000 | Cohen et al. | |
| 6,156,845 A | 12/2000 | Saito et al. | |
| 6,184,265 B1 | 2/2001 | Hamilton et al. | |
| 6,228,900 B1 | 5/2001 | Shen et al. | |
| 6,231,804 B1 | 5/2001 | Yamauchi et al. | |
| 6,245,276 B1 | 6/2001 | McNulty | |
| 6,277,390 B1 | 8/2001 | Schaffner | |
| 6,432,349 B1 | 8/2002 | Pletcher | |
| 6,437,048 B1 | 8/2002 | Saito et al. | |
| 6,448,315 B1 | 9/2002 | Lidgren et al. | |
| 6,464,926 B1 | 10/2002 | Merrill et al. | |
| 6,503,439 B1 | 1/2003 | Burstein | |
| 6,558,794 B1 | 5/2003 | Fehrenbacher | |
| 6,562,540 B2 | 5/2003 | Saum et al. | |
| 6,620,198 B2 | 9/2003 | Burstein et al. | |
| 6,627,141 B2 | 9/2003 | McNulty | |
| 6,641,617 B1 | 11/2003 | Merrill et al. | |
| 6,664,308 B2 | 12/2003 | Sun | |
| 6,664,317 B2 | 12/2003 | King, III | |
| 6,692,679 B1 | 2/2004 | McNulty | |
| 6,786,933 B2 | 9/2004 | Merrill et al. | |
| 6,818,020 B2 | 11/2004 | Sun | |
| 6,818,172 B2 | 11/2004 | King et al. | |
| 6,852,772 B2 | 2/2005 | Muratoglu et al. | |
| 6,853,772 B2 | 2/2005 | Battialo | |
| 6,872,764 B2 | 3/2005 | King, III | |
| 6,933,026 B2 | 8/2005 | Mauze | |
| 7,094,472 B2 | 8/2006 | DuPlessis et al. | |
| 7,160,492 B2 | 1/2007 | King | |
| 7,166,650 B2 | 1/2007 | Muratoglu et al. | |
| 7,214,764 B2 | 5/2007 | King | |
| 7,259,198 B2 | 8/2007 | Vaillant | |
| 7,304,097 B2 | 12/2007 | Muratoglu et al. | |
| 7,335,697 B2 | 2/2008 | King et al. | |
| 7,384,430 B2 | 6/2008 | Greer | |
| 7,431,874 B2 | 10/2008 | Muratoglu et al. | |
| 7,435,372 B2 | 10/2008 | Mimnaugh et al. | |
| 7,445,641 B1 | 11/2008 | Ornberg et al. | |
| 7,498,365 B2 | 3/2009 | Muratoglu et al. | |
| 7,507,774 B2 | 3/2009 | Muratoglu et al. | |
| 7,569,620 B2 | 8/2009 | Muratoglu et al. | |
| 7,615,075 B2 | 11/2009 | Kunze et al. | |
| 7,635,725 B2 * | 12/2009 | Bellare et al. | 522/161 |

(Continued)

FOREIGN PATENT DOCUMENTS

| | | |
|---|---|---|
| AU | 2006283596 A1 | 1/2007 |
| AU | 2006350369 A1 | 8/2008 |

(Continued)

OTHER PUBLICATIONS

US 7,253,214, 08/2007, McKellop (withdrawn).
"New Joint Replacement Material Developed at MGH put to first Clinic Use" news release from Massachusetts General Hospital, dated Jul. 23, 2007, accessed May 13, 2008.
"Joint Replacement Material Developed at the MGH" from MA General Hosp.MGH Hotline On-line publication dated Aug. 10, 2007.
E-Poly HXLPE Brochure from BioMet Orthopedics, dated 2007.
Wannomae, et al., "Vitamin E Stabilized, Irradiated UHMWPE for Cruciate Retaining Knee Components",, 53rd Annual Meeting of Orthopaedic Research Society,. Feb. 11-14, 2007 Poster No. 1783.
Kurtz, et al., "Trace Concentrations of Vitamin E Protect Radiation Crosslinked UHMWPE from Oxidative Degration", 53rd Annual Meeting of the Orthopaedic Research Society. Feb. 11-14, 2007, Paper No. 0020.
Bragdon, et al., "A New Pin-onDisk Wear Testing Method for Simulating Wear of Polyethylene on Cobalt-Chrome Alloy in Total Hip Arthroplasty", Journal of Arthroplasty, vol. 16 No. 5, 2001 pp. 658-665.
Wirtten Opinion & Search Report for PCT/US2009/032412 dated Mar. 25, 2010.
Written Opinion & Search Report for PCT/US/2008/059909 dated Sep. 14, 2009.
Written Opinion and Search Report for PCT/EP2005/008967 dated Jun. 21, 2006.

(Continued)

*Primary Examiner* — Nathan M Nutter
(74) *Attorney, Agent, or Firm* — Schwegman, Lundberg & Woessner P.A.

(57) ABSTRACT

The present invention generally provides implantable articles and methods of forming implantable articles from a crosslinked ultrahigh molecular weight polyethylene ("UHMWPE") blend stabilized with Vitamin E. The crosslinked UHMWPE blend may be prepared by combining the UHMWPE material and vitamin E prior to irradiating the UHMWPE blend with electron beam radiation at a sufficient radiation dose rate to induce crosslinking. The crosslinked UHMWPE blend may be incorporated into a variety of implants, and in particular, into endoprosthetic joint replacements.

24 Claims, 10 Drawing Sheets

U.S. PATENT DOCUMENTS

| | | | |
|---|---|---|---|
| 7,683,133 B2 * | 3/2010 | King et al. | 525/240 |
| 7,790,095 B2 * | 9/2010 | Muratoglu et al. | 264/488 |
| 7,806,064 B2 * | 10/2010 | Wellman | 114/67 R |
| 7,833,452 B2 * | 11/2010 | Muratoglu et al. | 264/235 |
| 7,846,376 B2 * | 12/2010 | Abt et al. | 264/494 |
| 7,863,348 B2 * | 1/2011 | Abt et al. | 523/113 |
| 8,129,440 B2 | 3/2012 | Rufner et al. | |
| 8,178,594 B2 | 5/2012 | Rufner et al. | |
| 2001/0027345 A1 | 10/2001 | Merrill et al. | |
| 2001/0049401 A1 | 12/2001 | Salovey et al. | |
| 2002/0007219 A1 | 1/2002 | Merrill et al. | |
| 2002/0156536 A1 | 10/2002 | Harris et al. | |
| 2003/0013781 A1 | 1/2003 | Merrill et al. | |
| 2003/0045603 A1 | 3/2003 | Salovey et al. | |
| 2003/0105182 A1 | 6/2003 | Merrill et al. | |
| 2003/0119935 A1 | 6/2003 | Merrill et al. | |
| 2003/0127778 A1 | 7/2003 | Scott et al. | |
| 2003/0149125 A1 | 8/2003 | Muratoglu | |
| 2003/0158287 A1 | 8/2003 | Salovey et al. | |
| 2003/0212161 A1 | 11/2003 | McKellop | |
| 2004/0051213 A1 | 3/2004 | Muratoglu | |
| 2004/0156879 A1 | 8/2004 | Muratoglu et al. | |
| 2004/0265165 A1 * | 12/2004 | King | 422/28 |
| 2005/0006821 A1 | 1/2005 | Merrill et al. | |
| 2005/0056971 A1 | 3/2005 | Merrill et al. | |
| 2005/0059750 A1 | 3/2005 | Sun et al. | |
| 2005/0096749 A1 | 5/2005 | Merrill et al. | |
| 2005/0124718 A1 | 6/2005 | Muratoglu et al. | |
| 2005/0125074 A1 | 6/2005 | Salovey et al. | |
| 2005/0146070 A1 | 7/2005 | Muratoglu et al. | |
| 2005/0165495 A1 | 7/2005 | Merrill et al. | |
| 2005/0194722 A1 | 9/2005 | Muratoglu et al. | |
| 2005/0194723 A1 | 9/2005 | Muratoglu et al. | |
| 2005/0267594 A1 | 12/2005 | Merrill et al. | |
| 2006/0079597 A1 | 4/2006 | Muratoglu et al. | |
| 2006/0115668 A1 | 6/2006 | King et al. | |
| 2006/0264541 A1 | 11/2006 | Lederer et al. | |
| 2007/0004818 A1 | 1/2007 | Muratoglu et al. | |
| 2007/0043137 A1 | 2/2007 | Muratoglu et al. | |
| 2007/0059334 A1 | 3/2007 | Abt et al. | |
| 2007/0077268 A1 | 4/2007 | King et al. | |
| 2007/0114702 A1 | 5/2007 | Muratoglu et al. | |
| 2007/0149660 A1 | 6/2007 | Kumer et al. | |
| 2007/0191504 A1 | 8/2007 | Muratoglu | |
| 2007/0232762 A1 | 10/2007 | Ernsberger et al. | |
| 2007/0265369 A1 | 11/2007 | Muratoglu et al. | |
| 2007/0267030 A1 | 11/2007 | Muratoglu et al. | |
| 2007/0275030 A1 | 11/2007 | Muratoglu et al. | |
| 2007/0293647 A1 | 12/2007 | McKellop et al. | |
| 2008/0039545 A1 | 2/2008 | Muratoglu et al. | |
| 2008/0067724 A1 | 3/2008 | Muratoglu et al. | |
| 2008/0090933 A1 | 4/2008 | Muratoglu et al. | |
| 2008/0090934 A1 | 4/2008 | Muratoglu et al. | |
| 2008/0119582 A1 | 5/2008 | Muratoglu et al. | |
| 2008/0133018 A1 | 6/2008 | Salovey et al. | |
| 2008/0133021 A1 | 6/2008 | Shen et al. | |
| 2008/0139137 A1 | 6/2008 | Guo et al. | |
| 2008/0140196 A1 | 6/2008 | Schroeder et al. | |
| 2008/0214692 A1 | 9/2008 | Muratoglu et al. | |
| 2008/0215142 A1 | 9/2008 | Muratoglu et al. | |
| 2008/0262120 A1 | 10/2008 | Muratoglu | |
| 2008/0274161 A1 | 11/2008 | Muratoglu et al. | |
| 2008/0293856 A1 | 11/2008 | Kumer et al. | |
| 2008/0319137 A1 | 12/2008 | Rufner et al. | |
| 2009/0030524 A1 | 1/2009 | Schroeder et al. | |
| 2009/0105364 A1 | 4/2009 | Merrill et al. | |
| 2009/0118390 A1 | 5/2009 | Abt et al. | |
| 2009/0192610 A1 | 7/2009 | Case et al. | |
| 2009/0265001 A1 | 10/2009 | Muratoglu et al. | |
| 2009/0281624 A1 | 11/2009 | Conteduca et al. | |
| 2010/0029858 A1 | 2/2010 | Rufner et al. | |
| 2010/0082101 A1 * | 4/2010 | Muratoglu et al. | 623/11.11 |
| 2010/0137481 A1 | 6/2010 | Shen et al. | |
| 2011/0028600 A1 | 2/2011 | Rufner et al. | |
| 2011/0306698 A1 | 12/2011 | Pletcher | |

FOREIGN PATENT DOCUMENTS

| | | |
|---|---|---|
| CA | 2619937 A1 | 3/2007 |
| CA | 2669386 A1 | 8/2008 |
| CS | 221403 | 4/1983 |
| CS | 221405 | 2/1986 |
| CZ | 221405 | 2/1986 |
| EP | 0560279 | 9/1993 |
| EP | 0727195 | 8/1996 |
| EP | 1421918 | 5/2004 |
| EP | 1647242 | 4/2006 |
| EP | 1924614 A2 | 5/2008 |
| EP | 2046577 A1 | 4/2009 |
| EP | 2083981 A1 | 5/2009 |
| EP | 2150285 B1 | 2/2012 |
| JP | 2012143575 A | 8/2012 |
| WO | WO-8900755 A1 | 1/1989 |
| WO | WO/01/05337 | 1/2001 |
| WO | WO/01/80778 | 11/2001 |
| WO | WO/03/049930 | 6/2003 |
| WO | WO/2004/024204 | 3/2004 |
| WO | WO/2004/064618 | 8/2004 |
| WO | WO/2004/101009 | 11/2004 |
| WO | WO/2007/019874 | 2/2007 |
| WO | WO-2007024684 A2 | 3/2007 |
| WO | WO/2007/056561 | 5/2007 |
| WO | WO/2007/121167 | 10/2007 |
| WO | WO-2008016174 A1 | 2/2008 |
| WO | WO-2008052574 A1 | 5/2008 |
| WO | WO/2008/092047 | 7/2008 |
| WO | WO/2008/101073 | 8/2008 |
| WO | WO/2008/101134 | 8/2008 |
| WO | WO/2008/113388 | 9/2008 |
| WO | WO/2008/124825 | 10/2008 |
| WO | WO-2008124825 A2 | 10/2008 |
| WO | WO/2009/032909 | 3/2009 |
| WO | WO/2009/045658 | 4/2009 |
| WO | WO 2010/129514 | 11/2010 |
| WO | WO-2010129514 A3 | 11/2010 |

OTHER PUBLICATIONS

Oral, et al., "Blending a-Tocopherol with UHMWPE Powder for Oxidation Resistance", 50th Annual Meeting of Orthopaedic Research Society, Poster No. 1485, 2005.

Oral, et al., "x-Tocopherol-doped irradiated UHMWPE for high fatigue resistance and low wear", Biomaterials, vol. 25, 2004, pp. 5515-5522.

Oral, et al., "Characterization of irradiated blends of X-tocopherol and UHMWPE", Biomaterials, vol. 26, 2005, pp. 6657-6663.

Parth, et al "Studies on the effect of electron beam radiation on the molecular structure of ultra-high molecular eight polyethylene under the influence of x-tocopherol w/ respect to its application in medical implants", Jrnl of Materials Science,vol. 13, 2002 pp. 917.

Tomita, et al., "Prevention of Fatigue Cracks in Ultrahigh Molecular Weight Polyethylene Joint Components by the Addition of Vitamin E", Applied Biomaterials, vol. 48, 1999, pp. 474-478.

Shibata, et al., "The anti-oxidative properties of x-tocopherol in y-irradiated UHMWPE with respect to fatigue and oxidation resistance", Biomaterials, vol. 26, 2005, pp. 5755-5762.

International Search Report for PCT/EP2009/008250 dated Jan. 21, 2010.

Extended EP Search Report and Written Opinion for EP Application No. 10 01 2579 dated Dec. 9, 2010.

Extended EP Search Report and Written Opinion for EP Application No. 10 01 2589 dated Dec. 9, 2010.

E. Oral, et al., Crosslinked Vitamin E blended UHMWPE with Improved Grafting and Wear Resistance, ORS 2011 Annual Meeting, Poster No. 1181.

C. Wolf, et al., Radiation grafting of Vitamin E to Ultra High Molecular Weight Polyethylene, ORS 2011 Annual Meeting, Poster No. 1178.

E. Oral, et al., Trace Amounts of Grafted Vitamin E Protect UHMWPE Against Squalene-Initiated Oxidation, ORS 2011 Annual Meeting, Poster No. 1295.

S. Rowell, et al., Detection of Vitamin E in Irradiated UHMWPE by UV-Visible Spectroscopy, ORS 2011 Annual Meeting, Poster No. 1186.

European Office Action for EP Application No. 10 012579.8 dated Sep. 14, 2011.
European Office Action for EP Application No. 09 013 154.1 dated Sep. 14, 2011.
Japanese Office Action for Japanese Patent Application No. 2008-526378 dated Sep. 6, 2011 with English translation.
Canadian Office Action for Canadian Patent Application No. 2,619,502 dated Nov. 4, 2011.
Kurtz, S, et al., "Trace Concentrations of Vitamin E Protect Radiation Crosslinked UHMWPE from Oxidative Degradation", 53rd Annual Meeting of the Orthopaedic Research Society,.Feb. Paper No. 0020, (Nov. 14, 2007), 1 pg.
Oral, et al., "Blending a-Tocopherol with UHMWPE Powder for Oxidation Resistance", Poster 1485, 50th Annual Meeting of Orthopaedic Research Society, San Francisco CA, Mar. 7-10, 2004, Transactions, vol. 29, (2004), 1 pg.
Oral, et al., "Characterization of Irradiated Blends of X-Tocopherol and UHMWPE", Biomaterials vol. 26, (2005), 6657-6663.
Oral, et al., "x-Tocopherol-doped irradiated UHMWPE for high fatigue resistance and low wear", Biomaterials vol. 25, (2004), 5515-5522.
U.S. Appl. No. 12/943,160, filed Nov. 10, 2010, Ultra High Molecular Weight Polyethylene Articles and Methods of Forming Ultra High Molecular Weight Polyethylene Articles.
U.S. Appl. No. 12/847,741, filed Jul. 30, 2010, Antioxidant Stabilized Crosslinked Ultra-High Molecular Weight Polyethylene for Medical Device Applications.
"U.S. Appl. No. 11/465,743, Advisory Action mailed Jul. 16, 2008", 5 pgs.
"U.S. Appl. No. 11/465,743, Advisory Action mailed Aug. 6, 2008", 6 pgs.
"U.S. Appl. No. 11/465,743, Advisory Action mailed Aug. 24, 2009", 6 pgs.
"U.S. Appl. No. 11/465,743, Amended Appeal Brief filed Mar. 10, 2010", 42 pgs.
"U.S. Appl. No. 11/465,743, Amended Appeal Brief filed Dec. 15, 2009", 41 pgs.
"U.S. Appl. No. 11/465,743, Appeal Brief filed Nov. 15, 2009", 41 pgs.
"U.S. Appl. No. 11/465,743, Final Office Action mailed May 1, 2008", 9 pgs.
"U.S. Appl. No. 11/465,743, Final Office Action mailed Jun. 16, 2009", 11 pgs.
"U.S. Appl. No. 11/465,743, Non Final Office Action mailed Sep. 28, 2007", 7 pgs.
"U.S. Appl. No. 11/465,743, Non Final Office Action mailed Dec. 15, 2008", 12 pgs.
"U.S. Appl. No. 11/465,743, Notice of Allowance mailed May 26, 2010", 6 pgs.
"U.S. Appl. No. 11/465,743, Notice of Allowance mailed Sep. 3, 2010", 7 pgs.
"U.S. Appl. No. 11/465,743, Response filed Jan. 17, 2008 to Non Final Office Action mailed Sep. 28, 2007", 13 pgs.
"U.S. Appl. No. 11/465,743, Response filed Mar. 16, 2009 to Non Final Office Action mailed Dec. 15, 2008", 11 pgs.
"U.S. Appl. No. 11/465,743, Response filed Jul. 1, 2008 to Final Office Action mailed May 1, 2008", 8 pgs.
"U.S. Appl. No. 11/465,743, Response filed Jul. 22, 2008 to Advisory Action mailed Jul. 16, 2008", 6 pgs.
"U.S. Appl. No. 11/465,743, Response filed Jul. 29, 2009 to Final Office Action mailed Jun. 16, 2009", 15 pgs.
"U.S. Appl. No. 11/465,743, Supplemental Notice of Allowability mailed Jul. 14, 2010", 2 pgs.
"U.S. Appl. No. 11/465,743, Supplemental Notice of Allowability mailed Sep. 23, 2010", 4 pgs.

"U.S. Appl. No. 11/465,743, Supplemental Notice of Allowability mailed Sep. 29, 2010", 4 pgs.
"U.S. Appl. No. 11/465,743, Supplemental Response filed Apr. 20, 2009 to Non Final Office Action mailed Dec. 15, 2008", 10 pgs.
"U.S. Appl. No. 12/262,531, Final Office Action mailed Jan. 14, 2010", 11 pgs.
"U.S. Appl. No. 12/262,531, Non Final Office Action mailed Jun. 17, 2010", 16 pgs.
"U.S. Appl. No. 12/262,531, Non Final Office Action mailed Jun. 25, 2009", 7 pgs.
"U.S. Appl. No. 12/262,531, Notice of Allowance mailed Oct. 28, 2010", 6 pgs.
"U.S. Appl. No. 12/262,531, Response filed Apr. 28, 2010 to Final Office Action mailed Jan. 14, 2010", 15 pgs.
"U.S. Appl. No. 12/262,531, Response filed Sep. 17, 2010 to Non Final Office Action mailed Jun. 17, 2010", 4 pgs.
"U.S. Appl. No. 12/262,531, Response filed Sep. 23, 2009 to Non Final Office Action mailed Jun. 25, 2009", 10 pgs.
"U.S. Appl. No. 12/262,531, Supplemental Notice of Allowability mailed Nov. 23, 2010", 4 pgs.
"U.S. Appl. No. 12/847,741, Response filed Sep. 26, 2012 to Final Office Action mailed Jun. 27, 2012", 14 pgs.
"U.S. Appl. No. 12/943,160, filed Nov. 10, 2010", 33 pgs.
"U.S. Appl. No. 12/943,160, Final Office Action mailed Sep. 28, 2012", 14 pgs.
"U.S. Appl. No. 12/943,160, Non Final Office Action mailed Mar. 16, 2012", 11 pgs.
"U.S. Appl. No. 12/943,160, Non Final Office Action mailed Aug. 12, 2011", 8 pgs.
"U.S. Appl. No. 12/943,160, Response filed Jan. 11, 2012 to Non Final Office Action mailed Aug. 12, 2011", 13 pgs.
"U.S. Appl. No. 12/943,160, Response filed Jul. 16, 2012 to Non Final Office Action mailed Mar. 16, 2012", 13 pgs.
"U.S. Appl. No. 12/943,160, Response filed Nov. 20, 2012 to Non Final Office Action mailed Sep. 28, 2012", 10 pgs.
"European Application Serial No. 09013154.1, European Search Report mailed Feb. 23, 2010", 6 pgs.
"European Application Serial No. 09013154.1, Office Action mailed Oct. 21, 2010", 1 pg.
"European Application Serial No. 09013154.1, Response filed Jan. 26, 2012 to Office Action mailed Sep. 14, 2011", 7 pgs.
"European Application Serial No. 09013154.1, Response filed Mar. 21, 2011 to Office Action mailed Oct. 21, 2010", 22 pgs.
"European Application Serial No. 10012579.8, Office Action mailed Sep. 18, 2012", 4 pgs.
"European Application Serial No. 10012589.7, Response filed Jan. 13, 2012", 8 pgs.
"European Application Serial No. 10012589.7, Response filed Feb. 13, 2012 to Office Action mailed Dec. 2, 2011", 7 pgs.
"International Application Serial No. PCT/EP2005/008967, International Preliminary Report on Patentability mailed Feb. 20, 2008", 7 pgs.
"International Application Serial No. PCT/EP2005/008967, International Search Report mailed Jun. 21, 2006", 3 pgs.
"International Application Serial No. PCT/EP2005/008967, Written Opinion mailed Jun. 21, 2006", 6 pgs.
"Japanese Application Serial No. 2008-526378, Office Action mailed Jun. 19, 2012", (w/ English translation), 6 pgs.
"Japanese Application Serial No. 2008-526378, Response filed Mar. 6, 2012 to Office Action mailed Sep. 6, 2011", (w/ English translation of claims), 10 pgs.
"Japanese Application Serial No. 2008-526378, Response filed Oct. 19, 2012 to Examiners Decision of Final Refusal mailed Jun. 19, 2012", (w/ English translation of claims), 13 pgs.
Pletcher, Dirk, et al., "Polymers Compositions Including an Antioxidant", U.S. Appl. No. 12/813,401, filed Jun. 10, 2010, 52 pgs.
Rufner, Alicia, et al., "U.S. Appl. No. 12/847,741, filed Jul. 30, 2010", 75 pgs.
"European Application Serial No. 09013154.1, European Examination Notification mailed Jan. 4, 2013", 4 pgs.
"European Application Serial No. 10012579.8, Response filed Jan. 28, 2013 to Examination Notification Art. 94(3) mailed Sep. 18, 2012", 9 pgs.
"Japanese Application Serial No. 2008-526378, Office Action mailed Dec. 18, 2012", (W/ English Translation), 4 pgs.

* cited by examiner

PRIOR ART

ULTRA HIGH MOLECULAR WEIGHT POLYETHYLENE ARTICLES AND METHODS OF FORMING ULTRA HIGH MOLECULAR WEIGHT POLYETHYLENE ARTICLES

CROSS REFERENCE TO RELATED ED APPLICATION

This application is a continuation of U.S. patent application Ser. No. 11/465,743, filed Aug. 18, 2006, and now, U.S. Pat. No. 7,846,376, which is a continuation of PCT Patent Application No. PCT/EP2005/008967, filed Aug. 18, 2005, both of which are incorporated herein by reference in their entireties as if completely set forth herein below.

BACKGROUND

Many endoprosthetic joint replacements currently implanted in patients include a highly polished metal or ceramic component articulating on an ultra high molecular weight polyethylene (UHMWPE) material or blend. Wear and abrasion resistance, coefficient of friction, impact strength, toughness, density, biocompatibility and biostability are some of the properties that make UHMWPE a suitable material for such implants. Although UHMWPE has been used in implants for many years, there is continuing interest in the wear and durability characteristics of implants incorporating UHMWPE.

One method employed to improve the durability and other physical characteristics of UHMWPE implants has been to expose such implants to radiation, for example gamma radiation or electron beam radiation, to induce crosslinking in the UHMWPE. Similar radiation sources have also been used to sterilize UHMWPE implants prior to distribution.

Despite the benefits of irradiating UHMWPE implants, the irradiation process may lead to increased rates of oxidation in the UHMWPE implant. In particular, irradiation has been shown to generate free radicals, which react in the presence of oxygen to form peroxyl radicals. These free radicals and peroxyl radicals may react with the polyethylene backbone and with each other to form oxidative degradation products and additional radical species. This cycle of oxidation product and radical species formation may occur over several years (both prior to and after implantation) as oxidation levels in the implant increase.

One method that has been utilized to reduce oxidation in irradiated UHMWPE materials is the addition of a stabilizing component to the UHMWPE material to inhibit the oxidation cycle. However, the addition of a stabilizer or stabilizing components, such as vitamin E, to UHMWPE prior to irradiation has been shown to have an adverse effect on crosslinking during irradiation. See Parth et al., "Studies on the effect of electron beam radiation on the molecular structure of ultrahigh molecular weight polyethylene under the influence of ct-tocopherol with respect to its application in medical implants," Journal of Materials Science Materials In Medicine, 13 (2002), pgs. 917-921.

For this reason, the addition of stabilizers to UHMWPE materials after forming and irradiating via diffusion has been proposed. See e.g., PCT Published Application No. WO 2004/101009. However, the addition of stabilizers after irradiation has several limitations. For example, vitamin E diffusion may provide a less uniform distribution of stabilizer in UHMWPE than pre-irradiation mixing. Diffusion of the vitamin E may also require separate irradiation steps to induce crosslinking prior to adding vitamin E and then to sterilize the implant after adding vitamin E.

Therefore, it would be beneficial to provide a method of forming a crosslinked UHMWPE material for use in implanted articles that overcomes one or more of these limitations.

SUMMARY

In one embodiment, the present invention provides an implantable article formed from a crosslinked ultrahigh molecular weight polyethylene ("UHMWPE") blend. The crosslinked UHMWPE blend may be prepared by combining a UHMWPE material with a stabilizer, such as vitamin E, and other optional additives reported herein to form a UHMWPE blend, and then by irradiating the UHMWPE blend with a suitable radiation source, such as electron beam radiation, at a sufficient radiation dose rate to induce crosslinking. The resulting crosslinked UHMWPE blend may have a swell ratio of less than about 4, and at least about 0.02 w/w % vitamin E is uniformly dispersed within at least a surface region of an article formed from the blend. According to this invention, the vitamin E may be uniformly distributed from the surface of the article to a depth of at least about 5 mm. The crosslinked UHMWPE blend of the present invention may be incorporated into a variety of implants, and in particular, into endoprosthetic joint replacements

DETAILED DESCRIPTION

UHMWPE is a semicrystalline, linear homopolymer of ethylene, which may be produced by stereospecific polymerization with a Ziegler-Natta catalyst at low pressure (6-8 bar) and low temperature (66-80° C.). The synthesis of nascent UHMWPE results in a fine granular powder. The molecular weight and its distribution can be controlled by process parameters such as temperature, time and pressure. UHMWPE generally has a molecular weight of at least about 2,000,000 g/mol.

Suitable UHMWPE materials for use as raw materials in the present invention may be in the form of a powder or mixture of powders. The UHMWPE material may be prepared almost entirely from UHMWPE powder, or may be formed by combining UHMWPE powder with other suitable polymer materials. In one embodiment, the UHMWPE material may include at least about 50 w/w % UHMWPE. Examples of suitable UHMWPE materials include GUR 1020 and GUR 1050 available from Ticona Engineering Polymers. Suitable polymer materials for use in combination with the UHMWPE materials may include disentangled polyethylene, high pressure crystallized polyethylene and various other "super tough" polyethylene derivatives. In addition, biocompatible non-polyethylene polymers may also be suitable for use in certain embodiments.

Suitable additives to the UHMWPE material include radiopaque materials, antimicrobial materials such as silver ions, antibiotics, and microparticles and/or nanoparticles serving various functions. Preservatives, colorants and other conventional additives may also be used.

Suitable stabilizers for addition to the UHMWPE material generally include materials that can be added in an effective amount to the UHMWPE material in order to, at least in part, inhibit the oxidation cycle caused by irradiation of UHMWPE. Vitamin E is particularly suitable for use in embodiments of the present invention. As used herein "vitamin E" refers generally to derivatives of tocopherol including a-tocopherol. Other suitable stabilizers may include phenolic antioxidants such as butylated hydroxytoluene, and ascorbic acid.

The vitamin E stabilizer and UHMWPE material may be combined via a number of known processes to form a UHMWPE blend. Such processes include physical mixing, mmixing with the aid of a solvent, mixing with the aid of a solvent (e.g. Co2) under supercritical temperature and pressure conditions, and ultrasonic mixing. Suitable mixing processes of these types are also described, for example, in U.S. Pat. Nos. 6,448,315 and 6,277,390, the disclosures of which are hereby incorporated by reference. In one embodiment, vitamin E is dissolved in ethanol and is drop-wise added to a powdered UHMWPE material while mixing. The ethanol may then be removed via a vacuum dryer or similar apparatus.

FIGS. 1A-1C and 2A-2B are flowcharts illustrating methods for preparing implants from. UHMWPE blends according to embodiments of the present invention. The general steps for processing the implant include a consolidating/compressing the UHMWPE blend, crosslinking the UHMWPE blend, manufacturing an implant from the compressed UHMWPE blend, packaging the implant, and sterilizing the packaged implant. As reflected in FIGS. 1 AC and 2A-2B, these steps may be carried out in varying order, in multiple steps, or simultaneously in accordance with embodiments of the present invention.

The UHMWPE blend may first be consolidated and/or compressed into suitable form for use as (or as part of) a prosthetic device or other implant. Suitable compression and/or consolidation techniques include, for example, compression molding, direct compression molding, hot isostatic pressing, ram extrusion, high pressure crystallization, injection molding, sintering or other conventional methods of compressing and/or consolidating UHMWPE. If desired, the compressed/consolidated UHMWPE blend may be further processed or manufactured by milling, machining, drilling, cutting, assembling with other components, and/or other manufacturing or pre-manufacturing steps conventionally employed to manufacture implants from UHMWPE.

Prior to and/or after processing the implant as reported above, the UHMWPE blend may be crosslinked by exposure to radiation at a high radiation dose and/or dose rate to form a crosslinked UHMWPE blend. In one embodiment, the UHMWPE blend may be exposed to electron beam radiation at a dose of at least about 25 kiloGrey, more particularly at least about 80 kiloGrey, and even more particularly at least about 95 kiloGrey. In another embodiment, the UHMWPE blend may be exposed to radiation at a dose rate of at least 1 MegaGrey per hour, more particularly at least about 15 MegaGrey per hour, and even more particularly about 18 MegaGrey per hour. In certain embodiments, the desired radiation dose may be achieved in a single exposure step at a high dose rate. In other embodiments, a series of high dose rate irradiation steps may be employed to expose the UHMWPE blend to a desired dose of radiation.

In certain embodiments, the radiation source is electron beam radiation. Electron beam radiation exposure may be performed using conventionally available electron beam accelerators. One commercial source for such an accelerator is IBA Technologies Group, Belgium. Suitable accelerators may produce an electron beam energy between about 2 and about 50 MeV, more particularly about 10 MeV, and are generally capable of accomplishing one or more of the radiation doses and/or dosage rates reported herein. Electron beam exposure may be carried out in a generally inert atmosphere, including for example, an argon, nitrogen, vacuum, or oxygen scavenger atmosphere. Exposure may also be carried out in air under ambient conditions according to one embodiment. Gamma and x-ray radiation may also be suitable for use in alternate embodiments of the invention. The present invention need is not necessarily limited to a specific type of source of radiation.

Optionally, prior to and/or after electron beam irradiation, the UHMWPE blend may be subjected to one or more temperature treatments. In one embodiment, the UHMWPE blend may be heated above room temperature, more particularly above about 100° C., even more particularly between about 120° C. and 130° C., prior to irradiation. U.S. Pat. No. 6,641,617 to Merril et al., which is hereby incorporated by reference, reports methods of employing such temperature treatment steps in greater detail. In another embodiment, the UHMWPE blend may remain at room temperature or may even be cooled below room temperature, for example, below the glass transition temperature of the UHMWPE blend. After irradiation, the crosslinked UHMWPE blend may be annealed at a temperature of up to about 200° C. for up to about 72 hours, more particularly at about 150° C. for about 5 hours. Alternatively or additionally, the crosslinked UHMWPE blend may be subjected to the mechanical annealing processes reported in U.S. Pat. No. 6,853,772 to Muratoglu, which is hereby incorporated by reference. In one embodiment, however, no pre- or post-irradiation temperature and/or annealing treatments are performed.

As part of the implant manufacturing process, additional components may be combined with the UHMWPE blend at any time during the process reported herein. In one embodiment, tribological components such as metal and/or ceramic articulating components and/or preassembled bipolar components may be joined with the UHMWPE blend. In other embodiments, metal backing (e.g. plates or shields) may be added. In further embodiments, surface components such a trabecular metal, fiber metal, beats, Sulmesh® coating, meshes, cancellous titanium, and/or metal or polymer coatings may be added to or joined with the UHMWPE blend. Still further, radiomarkers or radiopacifiers such as tantalum, steel and/or titanium balls, wires, bolts or pegs may be added. Further yet, locking features such as rings, bolts, pegs, snaps and/or cements/adhesives may be added. These additional components may be used to form sandwich implant designs, radiomarked implants, metal-backed implants to prevent direct bone contact, functional growth surfaces, and/or implants with locking features.

A variety of implants, and in particular endoprosthetic joint replacements, may be prepared by employing the methods reported herein. Examples of such implants include artificial hips and knees, cups or liners for artificial hips and knees, spinal replacement disks, artificial shoulder, elbow, feet, ankle and finger joints, mandibles, and bearings of artificial hearts.

After manufacturing of the implant has been completed, it may be packaged and sterilized prior to distribution. Packaging is generally carried out using either gas permeable packaging or barrier packaging utilizing a reduced oxygen atmosphere. Because the presence of vitamin E in the UHMWPE blend inhibits the oxidation cycle, conventional gas permeable packing may be suitable for embodiments of the present invention. Barrier packaging with an inert gas backfill (e.g. argon, nitrogen, oxygen scavenger) is also suitable.

As reflected in FIGS. 1A-1C and 2A-2B, sterilization may be accomplished either by radiation exposure during crosslinking of the UHMWPE blend, or as part of a separate processing step. A number of conventional sterilization techniques exist including gas plasma sterilization, ethylene oxide sterilization, gamma radiation sterilization and e-beam radiation. In the embodiments illustrated in FIGS. 1A, 1C and 2B, crosslinking is carried out prior to packaging. In the embodiments illustrated in FIGS. 1B and 2A, sterilization and crosslinking are carried out by e-beam irradiation in a single step after packaging the implant.

Sterilization generally occurs after packaging. In certain embodiments, sterilization is carried out at the same time as crosslinking, and therefore utilizes e-beam radiation. In embodiments in which crosslinking occurs before sterilization, additional suitable sterilization methods include gamma irradiation (either inert or in air), gas plasma exposure or ethylene oxide exposure.

As further exemplified in the Examples set forth below, the crosslinked UHMWPE blends produced according to embodiments of the present invention may have several beneficial characteristics. Notably, such blends exhibit lower levels of oxidation when compared to unstabilized UHMWPE materials, while still exhibiting suitable levels of crosslinking. The use of a high radiation dose rate or a series of high radiation dose rates, at least in part, contributes to improved crosslinking densities for the UHMWPE blend, which is contrary to prior art reports that suggest that suitable crosslinking densities are difficult to achieve when irradiating stabilized UHMWPE blends.

Also, such UHMWPE blends may have a generally uniform distribution of vitamin E at least a surface region of the blend. As used herein, the phrase "surface region" refers to a region of a crosslinked UHMWPE blend extending from a surface of the blend to some depth or range of depths below the surface. For example, the implants formed from the crosslinked UHMWPE blend of certain embodiments may exhibit a substantially uniform distribution of vitamin E to a surface depth of at least 3 mm, more particularly, at least 5 mm. Other embodiments may exhibit a substantially uniform distribution of vitamin E to a surface depth of at least 10 mm, more particularly at least 15 mm, even more particularly at least 20 mm. In further embodiments, the UHMWPE blend may have a substantially uniform distribution of vitamin E throughout the blend.

EXAMPLES

Table 1 sets forth the processing parameters for Samples A-I.

TABLE 1

| SAMPLE | Raw Material GUR | Vitamin E-Content w/w % | Preheating Before Irradiation ° C. | Irradiation Dose kGy | Irradiation Dose Rate | Irradiation Environment | Radiation Source | Annealing Process |
|---|---|---|---|---|---|---|---|---|
| A | 1020 | 0.0 | N/A | 25-40 | 0.5 to 10 (kGy/h) | $N_2$ | Gamma | N/A |
| B | 1020 | 0.0 | N/A | N/A | N/A | N/A | N/A | N/A |
| C | 1020 | 0.1 | N/A | N/A | N/A | N/A | N/A | N/A |
| D | 1020 | 0.1 | N/A | 25-40 | 0.5 to 10 (kGy/h) | $N_2$ | Gamma | N/A |
| E | 1020 | 0.0 | 120 | 95 | 18 (MGy/h) | Air | eBeam | 150° C., 5 h |
| F | 1020 | 0.1 | 120 | 95 | 18 (MGy/h) | Air | eBeam | 50° C., 5 h |
| G | 1020 | 0.1 | N/A | 95 | 18 (MGy/h) | Air | eBeam | N/A |
| H | 1020 | 0.1 | N/A | 95 | 0.5 to 10 (kGy/h) | Air | Gamma | N/A |
| I | 1050 | 0.0 | 120 | 95 | 18 (MGy/h) | Air | eBeam | 150° C. 5 h |

As set forth in Table 1, GUR 1020 and GUR 1050 brand UHMWPE powders are available from Ticona GmbH, FrankfurtMain, Del. The vitamin E used for Samples C, D and F-H was α-tocopherol obtained from DSM Nutritional Products AG, Basel, Switzerland.

For Samples C, D and F-H, the α-tocopherol was dissolved in ethanol in a concentration of 50 g/l and mixed into the UHMWPE drop-wise using a Nauta-Vrieco brand screw-cone mixer. The ethanol was then removed from the UHMWPE blend in a vacuum dryer at 50° C. for 6 hours, resulting in a UHMWPE blend having a concentration of α-tocopherol of about 0.1 w/w %, The resulting UHMWPE blend was then sintered for 7 hours at 220° C. and 35 bar to produce UHMWPE plates having a thickness of 60 mm and a diameter of 600 mm. Homogeneity of the α-tocopherol in the UHMWPE blend was measured by standard HPLC methods and determined to vary up to +/−2% from the desired content.

Samples A, D and H were irradiated using a Studer IR-168 Gamma Irradiator utilizing a $Co^{60}$ radiation source. Samples E-G and I were irradiated using a 10 MeV Rhodotron electron accelerator available from IBA SA, Louvain-La-Neuve using a 120 kW power setting.

Results

Figure 1A:
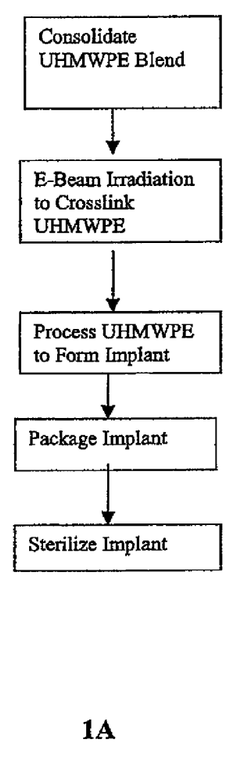
FIGS. 1A-1C are flow-charts illustrating methods of preparing UHMWPE implants according to embodiments of the present invention.
Figure 1B:
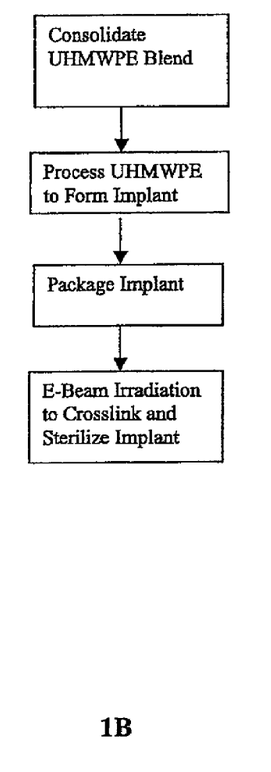
Figure 1C:
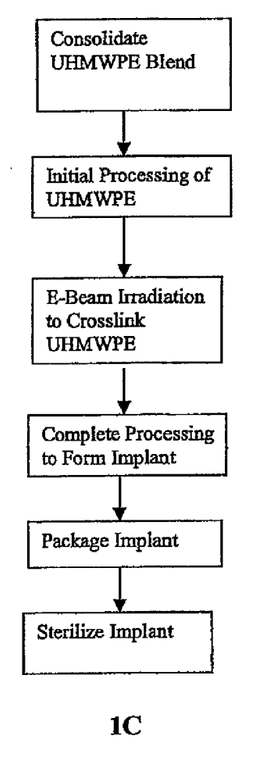
Figure 2A:
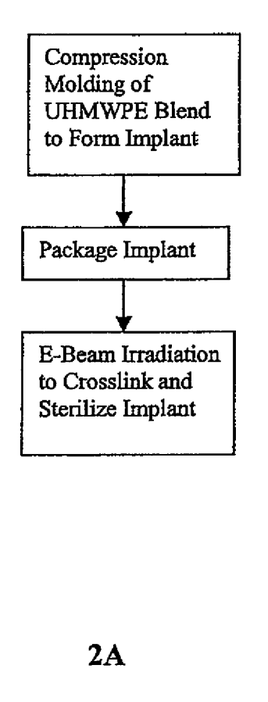
FIGS. 2A-2B are flow-charts illustrating methods of preparing UHMWPE implants according to additional embodiments of the present invention.
Figure 2B:
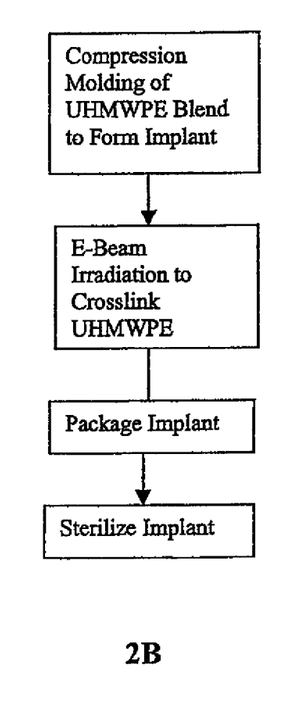
Figure 3:
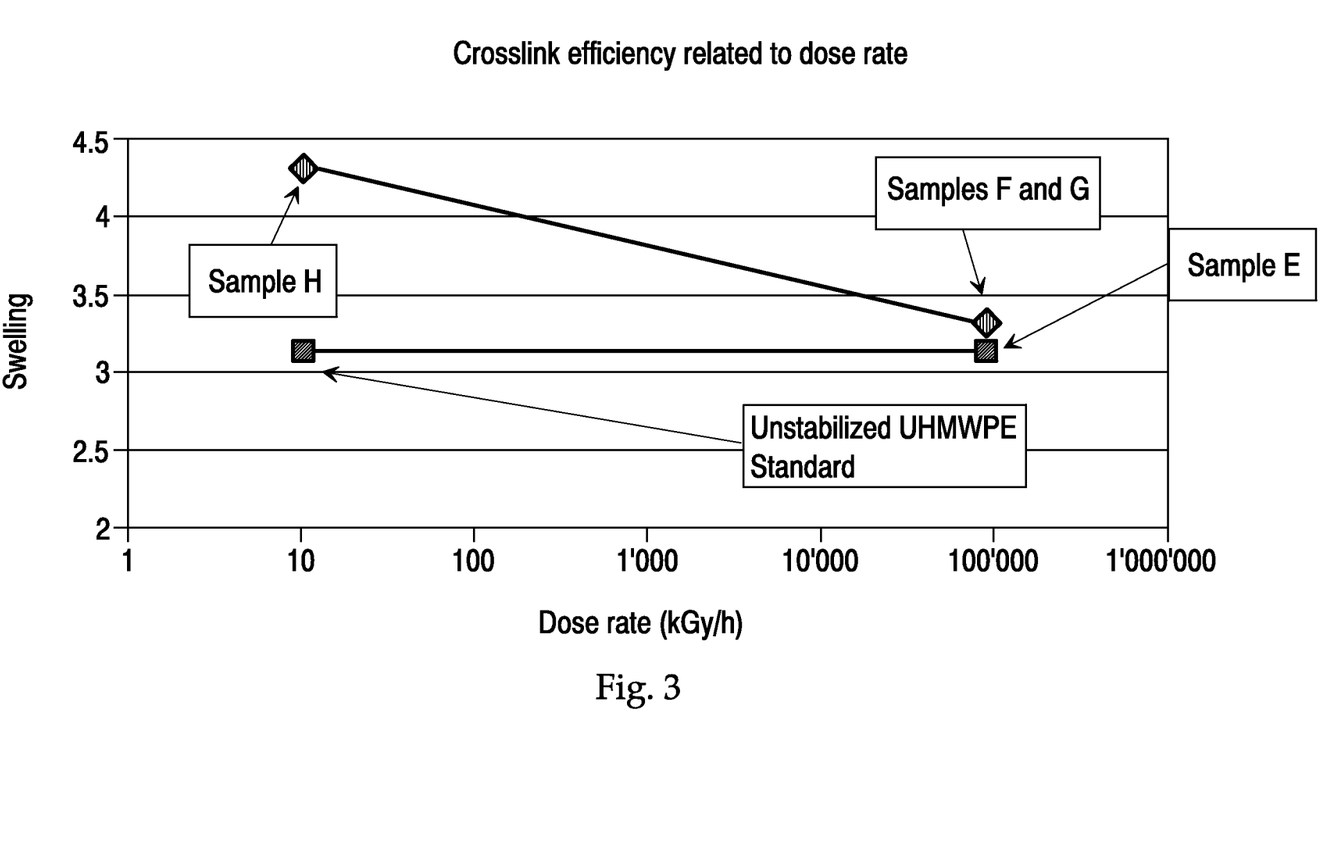
FIG. 3 is a line graph illustrating the swell ratio of several UHMWPE samples, described in the Example, at various radiation dose rates.

FIG. 3 shows a line graph illustrating the swell ratio of unstabilized polyethylene versus a polyethylene blend stabilized with Vitamin E. The swell ratio is a useful indicator of the crosslinking density of a particular material. In particular, lower relative swell ratios are indicative of higher levels of crosslinking, and vice versa. The swell ratio was determined according to ASTM F2214-02. Specifically, 4-6 mm cubes of each of Samples H, F, G and E were placed in a container filled with o-Xylene at 25° C. and placed in a dynamical mechanical analyzer (DMA, DMA 7e available from Perkin Elmer) for 10 minutes. A first sample height (Ho) was then taken for each sample. The samples were then heated at a rate of 5K/min to a maintained temperature of 130° C. A second sample height (Hf) was then taken after 120 minutes at 130° C. The swell ratio was then calculated according to the following equation:

$$q_s = (Ht/Ho)^3$$

The data points for the lower flat line include a swell ratio standard for unstabilized UHMWPE (obtained from the interlaboratory comparison in ASTM F2214-02 at a dose rate of 89 kGy) and unstabilized Sample E. These data points indicate that dose rates do not have a substantial effect on crosslink density. The data points for the upper descending line include Samples H, F and G. Notably, the increased irradiation dosage rates used for Samples F and G resulted in a decreased swell ratio when compared to sample H, and consequently, an increased crosslink density.

Figure 4A:
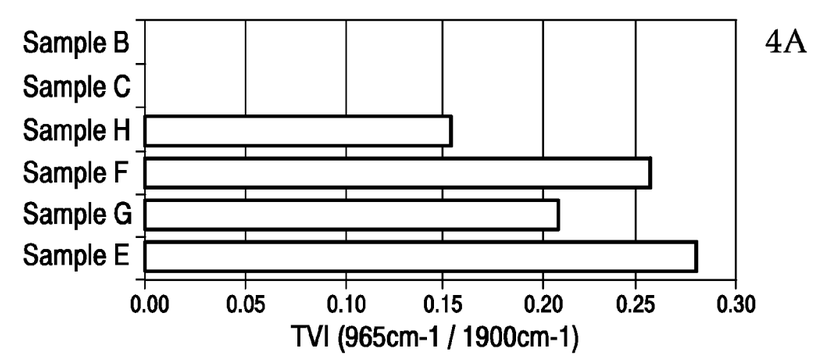
FIGS. 4A-4C are bar graphs illustrating the TVI (4A), swell ratio (4B) and soluble fraction (4C), of several UHMWPE samples.
Figure 4B:
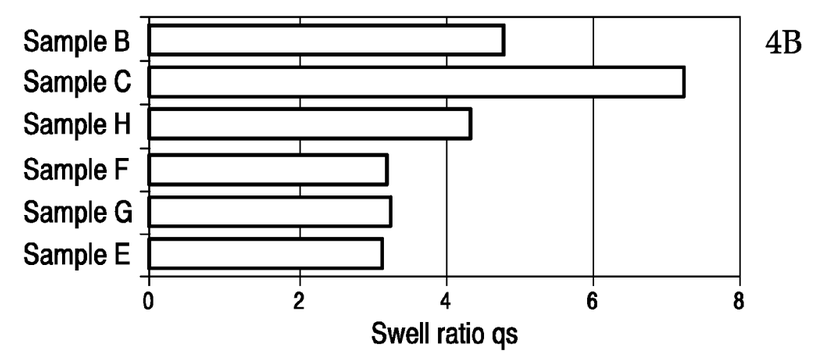
Figure 4C:
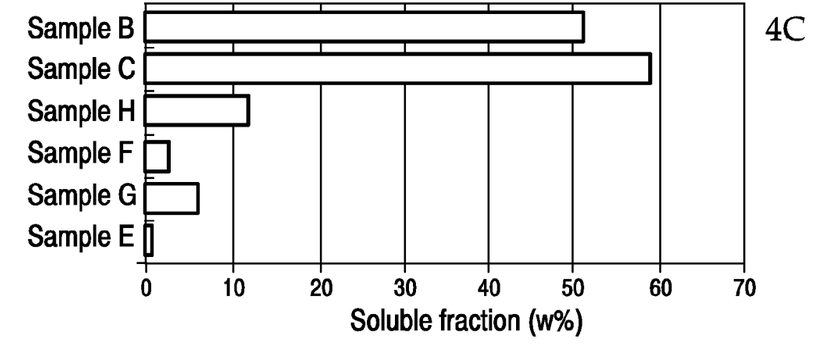

FIGS. 4A-4C are three bar graphs illustrating several characteristics of Samples 13, C, and E-H. FIG. 4A is a bar graph illustrating the trans-Vinylene Index (TVI) levels of the Samples. The TVI was determined by the method described in Muratoglu et al., "Identification and quantification of irradiation in UHMWPE through trans-vinylene yield." TVI levels are an indicator of the radiation absorption efficiency of UHMWPE. FIG. 4A indicates that the Samples E and F, which were preheated before irradiation and annealed after irradiation, possessed higher radiation absorption efficiency than other samples.

FIG. 4B is a bar graph illustrating the swell ratio of the same samples reported in FIG. 4A. Notably, Sample H, which was gamma-irradiated, shows a higher swell ratio (and therefore lower crosslink density) than the e-beam irradiated Samples E, F and G.

FIG. 4C is a bar graph of the soluble fraction of the samples reported in FIG. 4A. The soluble fraction indicates the percentage of fully crosslinked material in the sample. The soluble fraction for each sample was determined in accordance with ASTM 2765-01. Specifically, powdered UHMWPE was taken from a location 10 mm under the surface of the sample by a rasping technique. This sample was then weighed in a wire mesh and backfluxed for 12 hours in xylene. After backfluxing, the remaining gel portion was placed in a vacuum furnace and dried at a temperature of 140° C. and a pressure of less than 200 mbar, and was then conditioned in an exsiccator before being weighted again. The resulting gel portion and soluble portion was computed by weighing the sample before and after the procedure. Sample H, which was gamma irradiated, shows a higher soluble fraction than e-beam irradiated Samples E, F and G.

Figure 5:
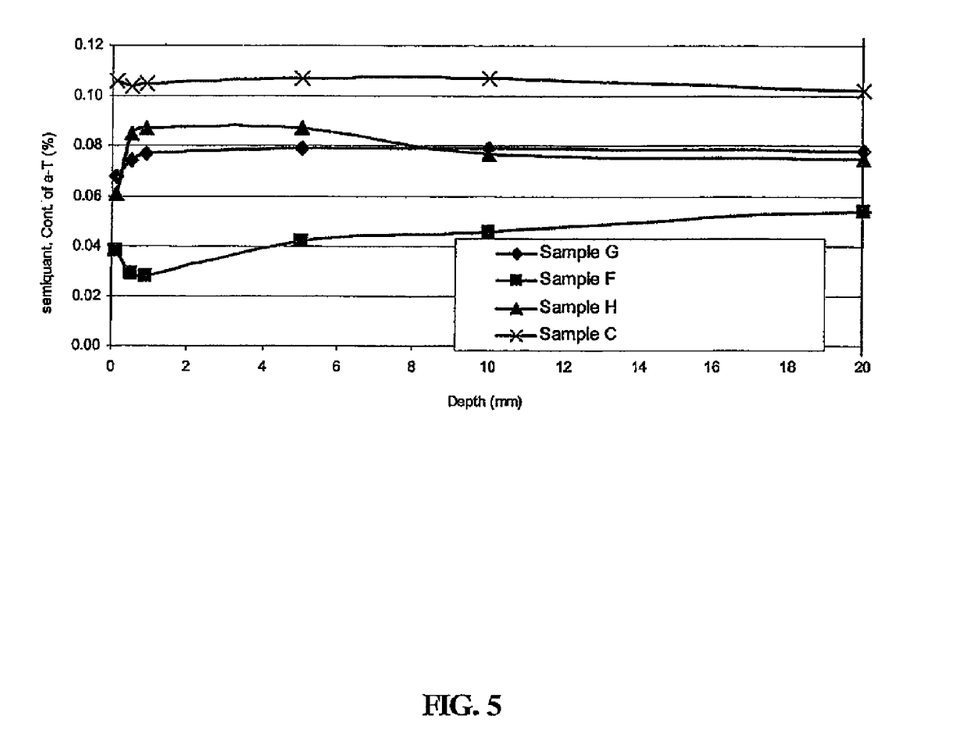
FIG. 5 is a line graph illustrating the vitamin E concentration of several UHMWPE samples at a range of depths.
Figure 6:
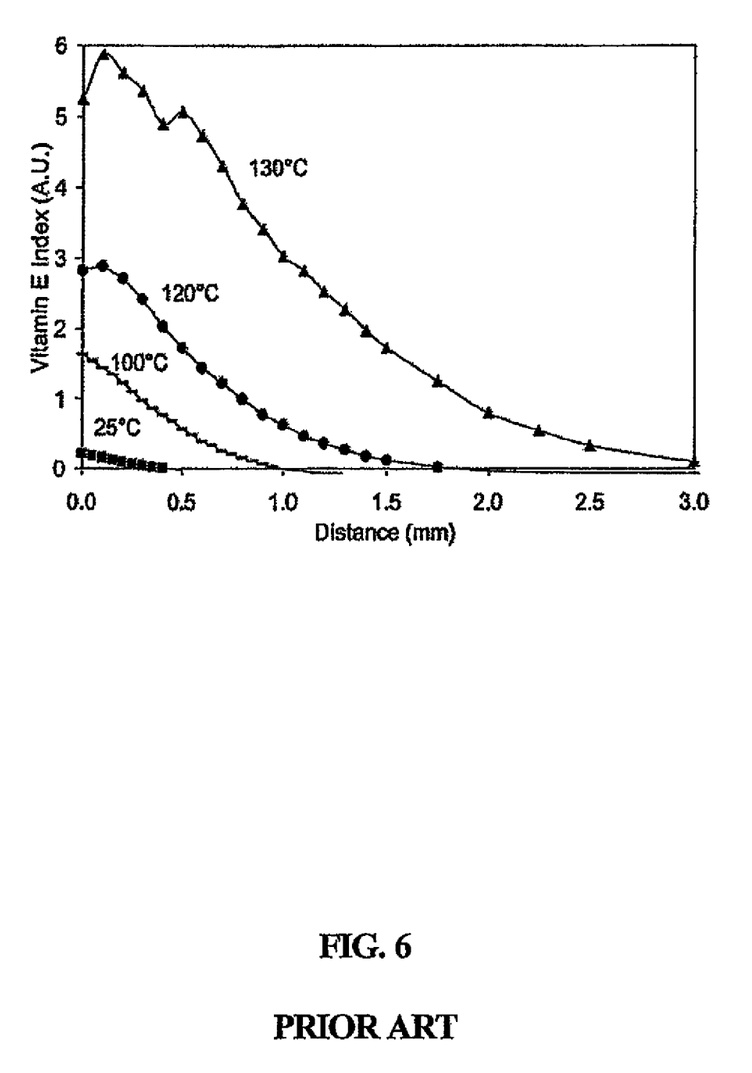
FIG. 6 is a prior art line graph showing the vitamin E index of samples prepared pursuant to U.S. Published Application No. 2004/0156879.

FIG. 5 is a line graph indicating the vitamin E content at a range of depths from the surface of Samples C, F, G and H. FIG. 5 indicates that a uniform vitamin E concentration is maintained in each Sample in a surface region at least up to the measured depth of 20 arum. This uniform distribution of vitamin E is particularly notable when compared to Prior Art FIG. 6 reported in U.S. Published Application No 2004/0156879, in which the vitamin E index of diffused vitamin E samples steadily decreased as depth increased.

Figure 7:
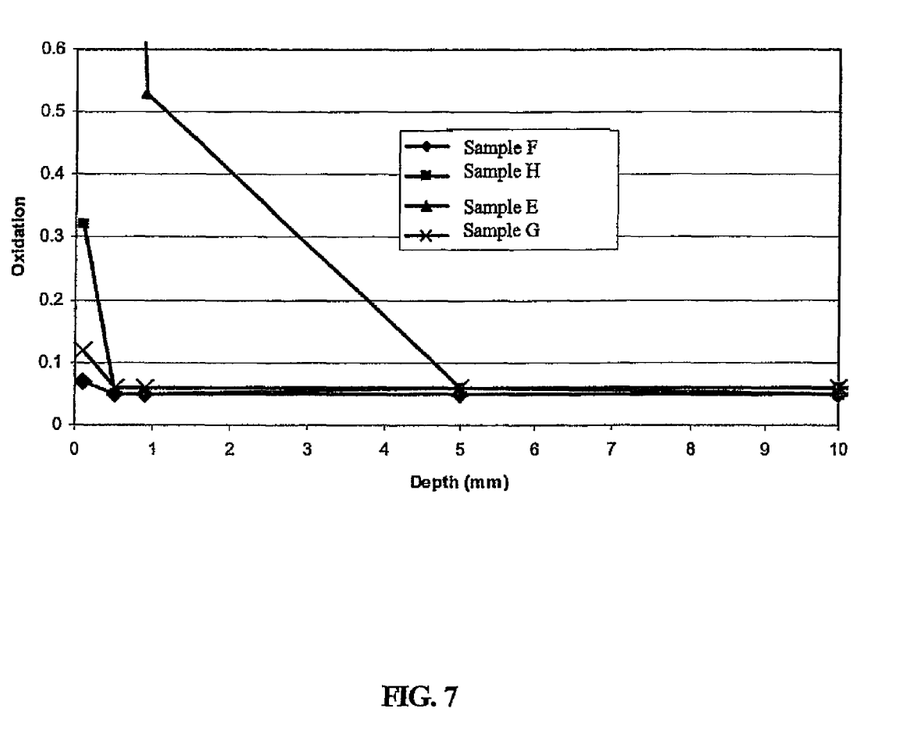
FIG. 7 is a line graph showing the oxidation levels of several UHMWPE samples at a range of depths.

FIG. 7 is a line graph illustrating the oxidation levels of Samples E, F, G and H. Notably, oxidation levels at certain depths from the surface of the sample material were higher for Sample E (did not include vitamin E) and Sample H (gamma irradiated) as compared to Samples G and F (e-beam irradiated).

Figure 8:
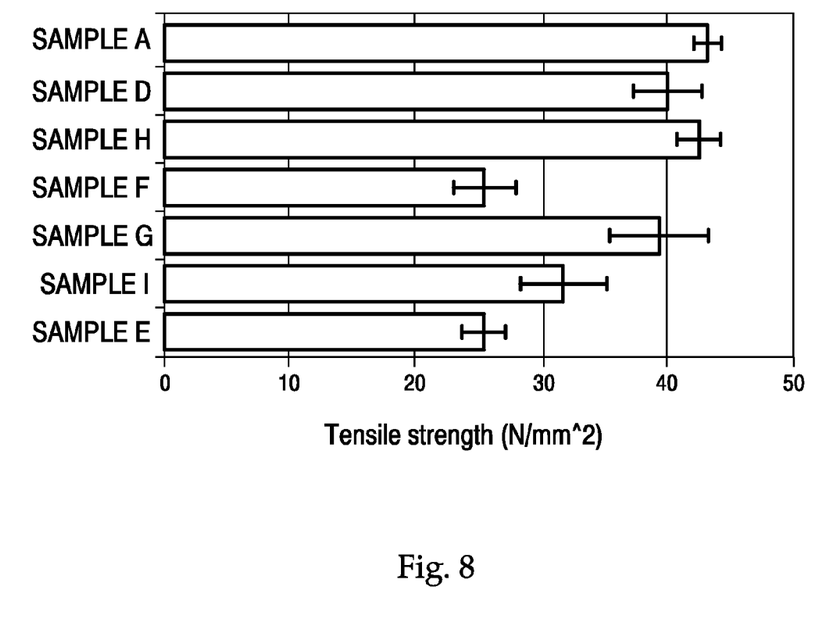
FIG. 8 is a bar graph showing the tensile strength of several UHMWPE samples.
Figure 9:
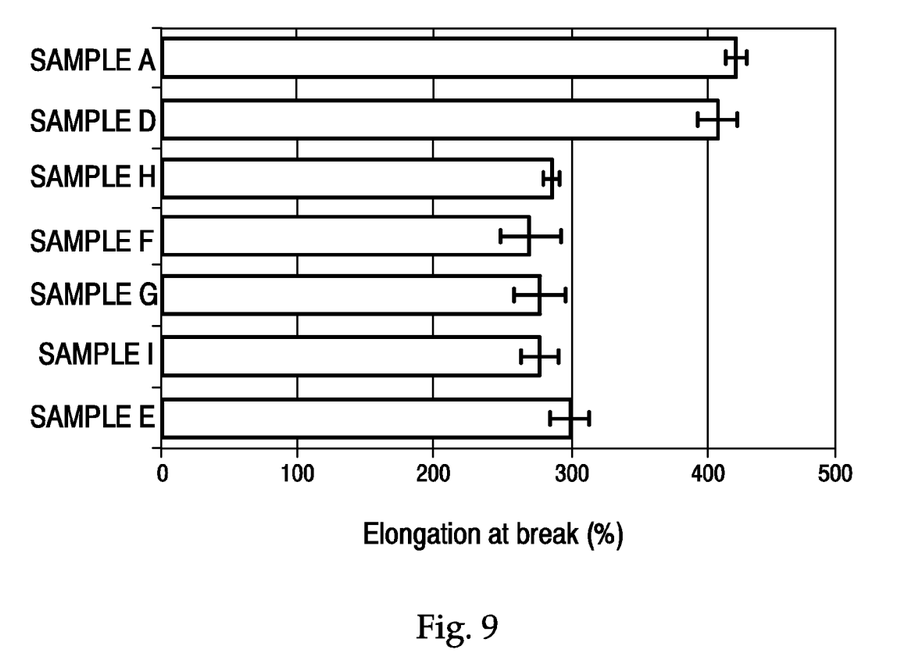
FIG. 9 is a bar graph showing the elongation percent at break of several UHMWPE samples.
Figure 10:
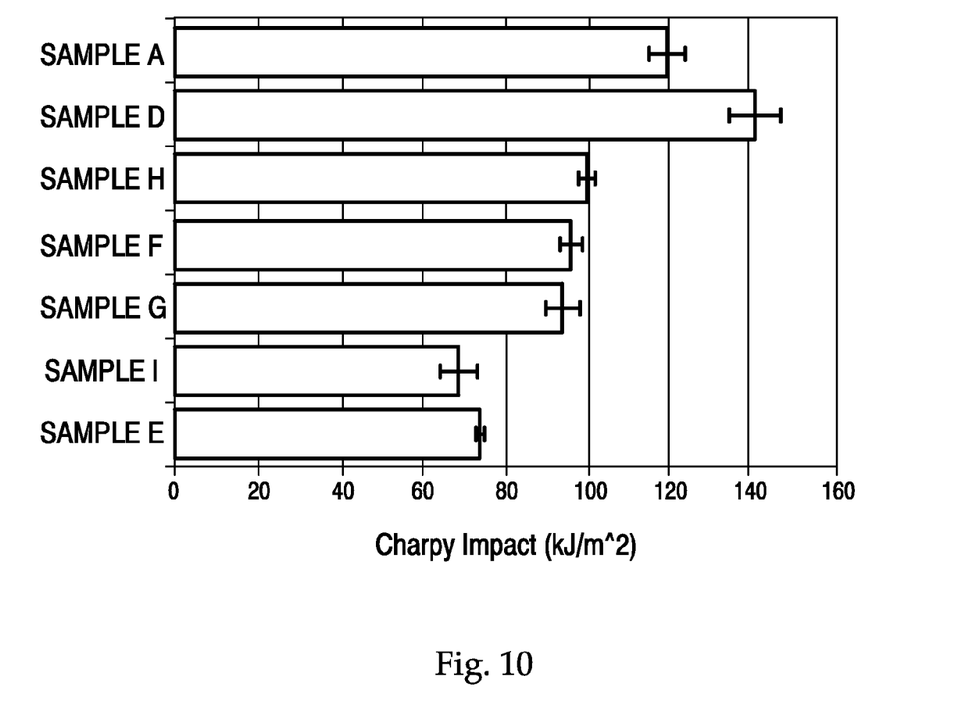
FIG. 10 is a bar graph showing the Charpy impact strength of several UHMWPE samples.

FIGS. 8-10 are a series of bar graphs illustrating various mechanical properties of Samples A, D, E, F, G, H and I. FIG. 8 illustrates the mechanical strength of each sample, and generally indicates that the pre-heating and annealing processing methods utilized with samples E, F and I resulted in somewhat decreased mechanical strength as compared to the cold irradiation method used for Sample G and H. FIG. 9 illustrates the elongation percent at the breaking point of each sample. FIG. 10 illustrates the impact strength of each sample based on the Charpy impact scale (kJ/m$^2$), and generally indicates that the presence of vitamin E increases the impact strength of crosslinked UHMWPE.

What is claimed:

1. A method of forming a crosslinked ultrahigh molecular weight polyethylene blend, comprising:
   combining ultrahigh molecular weight polyethylene with an amount of vitamin E to form an ultrahigh molecular weight polyethylene blend;
   consolidating the ultrahigh molecular weight polyethylene blend;
   preheating the consolidated ultrahigh molecular weight polyethylene blend; and
   irradiating the preheated consolidated ultrahigh molecular weight polyethylene blend using electron beam irradiation at an absorbed dose of at least about 60 kiloGrey and a dose rate of at least about 18 MegaGrey per hour to crosslink the consolidated ultrahigh molecular weight polyethylene blend.

2. The method of claim 1 wherein the vitamin E is dispersed substantially uniformly throughout the blend.

3. The method of claim 1 wherein the amount of vitamin E combined with the blend is between about 0.02 w/w % and about 2.0 w/w %.

4. The method of claim 1 wherein the amount of vitamin E combined with the blend is between about 0.05 w/w % and about 0.4 w/w %.

5. The method of claim 1 wherein the blend further comprises at least one additional polymer material.

6. The method of claim 1 wherein the consolidated ultrahigh molecular weight polyethylene blend is preheated above room temperature.

7. The method of claim 1 wherein the consolidated ultrahigh molecular weight polyethylene blend is preheated above 100° C.

8. The method of claim 1 wherein the consolidated ultrahigh molecular weight polyethylene blend is preheated to between about 120° C. and about 130° C.

9. The method of claim 1 further including annealing the irradiated consolidated ultrahigh molecular weight polyethylene blend at a temperature up to 200° C.

10. The method of claim 1 further including annealing the irradiated consolidated ultrahigh molecular weight polyethylene blend at a temperature up to 150° C.

11. The method of claim 1 further including annealing the irradiated consolidated ultrahigh molecular weight polyethylene blend at a temperature up to 50° C.

12. The method of claim 1 wherein the consolidated ultrahigh molecular weight polyethylene blend is irradiated with electron beam radiation at an absorbed dose of at least about 95 kiloGrey to form the crosslinked ultrahigh molecular weight polyethylene blend.

13. An implantable article, comprising: a crosslinked ultrahigh molecular weight polyethylene blend, wherein the blend is produced by:
  combining ultrahigh molecular weight polyethylene with vitamin E to form an ultrahigh molecular weight polyethylene blend;
  consolidating the ultrahigh molecular weight polyethylene blend;
  preheating the consolidated ultrahigh molecular weight polyethylene blend;
  irradiating the preheated consolidated ultrahigh molecular weight polyethylene blend using electron beam irradiation at an absorbed dose of at least about 60 kiloGrey and a dose rate of at least about 18 MegaGrey per hour to crosslink the consolidated ultrahigh molecular weight polyethylene blend; and,
  annealing the crosslinked consolidated ultrahigh molecular weight polyethylene blend.

14. The implantable article of claim 13 wherein the vitamin E is dispersed substantially uniformly throughout the blend.

15. The implantable article of claim 13 wherein the amount of vitamin E combined with the blend is between about 0.02 w/w % and about 2.0 w/w %.

16. The implantable article of claim 13 wherein the amount of vitamin E combined with the blend is between about 0.05 w/w % and about 0.4 w/w %.

17. The implantable article of claim 13 wherein the blend further comprises at least one additional polymer material.

18. The implantable article of claim 13 wherein the consolidated ultrahigh molecular weight polyethylene blend is preheated above room temperature.

19. The implantable article of claim 13 wherein the consolidated ultrahigh molecular weight polyethylene blend is preheated above 100° C.

20. The implantable article of claim 13 wherein the consolidated ultrahigh molecular weight polyethylene blend is preheated to between about 120° C. and about 130° C.

21. The implantable article of claim 13 further including annealing the irradiated consolidated ultrahigh molecular weight polyethylene blend at a temperature up to 200° C.

22. The implantable article of claim 13 further including annealing the irradiated consolidated ultrahigh molecular weight polyethylene blend at a temperature up to 150° C.

23. The implantable article of claim 13 further including annealing the irradiated consolidated ultrahigh molecular weight polyethylene blend at a temperature up to 50° C.

24. The implantable article of claim 13 wherein the consolidated ultrahigh molecular weight polyethylene blend is irradiated with electron beam radiation at an absorbed dose of at least about 95 kiloGrey to form the crosslinked ultrahigh molecular weight polyethylene blend.

* * * * *

UNITED STATES PATENT AND TRADEMARK OFFICE
CERTIFICATE OF CORRECTION

PATENT NO. : 8,470,903 B2
APPLICATION NO. : 12/942703
DATED : June 25, 2013
INVENTOR(S) : Abt et al.

It is certified that error appears in the above-identified patent and that said Letters Patent is hereby corrected as shown below:

On the title page, in column 2, under "Other Publications", line 16, delete "onDisk" and insert --on-Disk--, therefor On title page 2, in column 2, under "Foreign Patent Documents", line 2, after "CA 2669386 A1 8/2008", insert --¶CA 2619502 C 11/2012--, therefor On title page 2, in column 2, under "Other Publications", line 1, delete "a" and insert --α--, therefor On title page 2, in column 2, under "Other Publications", line 4, delete "x" and insert --α--, therefor On title page 2, in column 2, under "Other Publications", line 7, delete "X" and insert --α--, therefor On title page 2, in column 2, under "Other Publications", line 11, delete "x" and insert --α--, therefor On title page 2, in column 2, under "Other Publications", line 16, delete "x" and insert --α--, therefor On title page 2, in column 2, under "Other Publications", line 17, delete "y" and insert --γ--, therefor On title page 3, in column 1, under "Other Publications", line 13, delete "a" and insert --α--, therefor

On title page 3, in column 1, under "Other Publications", line 17, delete "X" and insert --α--, therefor On title page 3, in column 1, under "Other Publications", line 19, delete "x" and insert --α--, therefor In the Specification In column 1, line 6, after "RELATED", delete "ED", therefor Signed and Sealed this
Thirteenth Day of January, 2015

Michelle K. Lee
*Deputy Director of the United States Patent and Trademark Office*

CERTIFICATE OF CORRECTION (continued)
U.S. Pat. No. 8,470,903 B2

In column 1, line 55, delete "ct" and insert --α--, therefor

In column 1, line 56, delete "Science" and insert --Science:--, therefor

In column 3, line 42, delete "from." and insert --from--, therefor

In column 7, line 31, delete "13," and insert --B,--, therefor

In column 7, line 66, delete "arum." and insert --mm.--, therefor

In the Claims

In column 9, line 19, in Claim 13, delete "and," and insert --and--, therefor